United States Patent [19]
Gordon et al.

[11] Patent Number: 5,808,376
[45] Date of Patent: Sep. 15, 1998

[54] METHOD OF AND APPARATUS FOR POWER MANAGEMENT AND DISTRIBUTION IN A MEDICAL IMAGING SYSTEM

[75] Inventors: Bernard M. Gordon, Magnolia; Iosif Izrailit, Newton, both of Mass.

[73] Assignee: Analogic Corporation, Peabody, Mass.

[21] Appl. No.: 877,972

[22] Filed: Jun. 18, 1997

Related U.S. Application Data

[63] Continuation of Ser. No. 548,383, Nov. 28, 1995, which is a continuation of Ser. No. 345,493, Nov. 28, 1994, abandoned.

[51] Int. Cl.⁶ .................................................. H05G 1/02
[52] U.S. Cl. ............................ 307/66; 307/64; 307/72; 307/85; 307/86; 364/492; 378/101; 378/103; 378/107; 378/112
[58] Field of Search ................................ 378/101, 102, 378/103, 104, 107, 109, 110, 111, 112; 307/64, 66, 72, 73, 43, 44, 46, 48, 80, 85, 86, 87; 364/492; 363/89, 92

[56] References Cited

U.S. PATENT DOCUMENTS

| | | |
|---|---|---|
| Re. 34,379 | 9/1993 | Gordon ................................ 378/20 |
| 4,517,472 | 5/1985 | Ruitberg ............................... 307/82 |
| 4,860,185 | 8/1989 | Brewer et al. ........................ 307/66 |
| 4,928,283 | 5/1990 | Gordon ................................ 378/20 |
| 5,135,533 | 8/1992 | Stich ..................................... 307/66 |
| 5,226,064 | 7/1993 | Yahata et al. ...................... 378/101 |
| 5,347,164 | 9/1994 | Yen ...................................... 307/66 |
| 5,371,665 | 12/1994 | Quisenberry ......................... 363/89 |
| 5,461,263 | 10/1995 | Helfrich ................................ 307/64 |

Primary Examiner—William M. Shoop, Jr.
Assistant Examiner—Peter Ganjian
Attorney, Agent, or Firm—Lappin & Kusmer LLP

[57] ABSTRACT

An apparatus for energizing a large scale medical imaging system, preferably in the form of a CT scanner so that the scanner operates off an uninterruptable power supply in the event that the external power falls below sufficient power to operate the system so that system operation remains uninterruptable. The system is designed to operate off a broad range and types of external power supplies including those providing DC, single or three phase AC power. The system therefore can operate from a common single phase AC outlet. In addition, power factor correction is provided so that the system can correct for phase differences between the voltage and current at the input line created by the input impedance of the system.

29 Claims, 4 Drawing Sheets

METHOD OF AND APPARATUS FOR POWER MANAGEMENT AND DISTRIBUTION IN A MEDICAL IMAGING SYSTEM

CROSS-REFERENCE TO RELATED APPLICATIONS

This is a continuation of application Ser. No. 08/548,383 filed on Nov. 28, 1995, which is a continuation of U.S. patent application Ser. No. 08/345,493, entitled Method of and Apparatus for Power Management and Distribution in a Medical Imaging System, filed on Nov. 28, 1994, and assigned to the present assignee (Attorney's Docket No. ANA-027) now abandoned.

FIELD OF THE INVENTION

This invention relates generally to medical imaging systems, and more particularly to power management and distribution in large scale medical imaging systems.

BACKGROUND OF THE INVENTION

As the term is used herein "large scale medical imaging systems" refers to such systems as computed tomography (CT) systems, magnetic resonance imaging (MRI) systems, positron emission tomography (PET) systems, and the like, and excludes small imaging systems, such as portable X-ray machines. Present large scale medical imaging systems typically have high power requirements. Since a standard wall $110^V$ AC outlet, such as one commonly found in a home or office, does not usually provide enough power to operate such medical imaging systems, a special high power electrical outlet, such as a three phase AC outlet, is usually required. Consequently, in settings where a high power electrical outlet is not available, such as some rural hospitals or health facilities in lesser developed countries, such known large scale medical imaging systems cannot be easily used, if they can be used at all. Thus, a large scale medical imaging system that can operate using a standard electrical outlet would be highly advantageous.

Further, in some lesser developed countries, or in developed countries during periods of power shortages, even standard electrical outlets cannot be relied upon to dependably supply electrical power. For example, the power supplied may be below a normal operating threshold, such as during a "brown out", power may be interrupted completely, or power may be interrupted during a phase of each cycle. In any case, normal operation of a large scale medical imaging device would be seriously impaired or interrupted. Moreover, present x-ray equipment is extremely sensitive to line fluctuations.

Additionally, many present large scale medical imaging systems exhibit a non-unity power factor, resulting in an impedance load on the input line and therefore inefficient and excessive power consumption. Since known power factor correction devices are difficult to use with such large scale medical imaging equipment due to the high power (e.g., 10 Kilowatts to 40 Kilowatts) that such medical imaging equipment requires, the power efficiency of present medical imaging equipment is less than ideal.

Many present large scale medical imaging systems, such as CT scanners, include a rotating imaging subsystem that requires electrical power. To provide power to a rotating imaging subsystem, it is known to use electromechanical slip rings. However, over long periods of use, mechanical wear and foreign object contamination can occur, leading to reduced electromechanical contact reliability, possibly resulting in momentary loss of power. The use of slip rings for delivering power to the rotating sub-system also introduces electrical noise. In addition, a product that incorporates a large rotating disk for supporting at least a part of the imaging subsystem, such as a CT scanner, requires the use of commensurately large slip rings, thereby adding significant weight to the total weight of the system.

It is also known to provide electrical power to the rotating part of the imaging subsystem using direct connection with cables. Again, disadvantages include significant additional weight due to the use of cables, and decreased reliability due to, for example, the vulnerability of cables to disconnection and breakage when the cables are repeatedly wound or overwound. Also, the cables must be periodically rewound, thereby preventing continuous rotation of a scanning disk in the same direction for extended periods of time, as is desirable in CT scan applications.

Further, present large scale medical imaging systems are so large as to require specially-sized entryways for allowing a system to be moved into and mounted for use in a particular room. Consequently, present systems can be used only in rooms having a sufficiently wide doorway, often making it necessary for the patient to come to the machine, when it would be more advantageous for the machine to be brought to the patient.

An improved CT scanner, suggested in U.S. Pat. No. 4,928,283 and U.S. Patent Reissue No. 34,379 reissued to Bernard Gordon on Sep. 14, 1993, eliminates slip rings and cables and is designed to use batteries for powering at least a part of the CT scanner and to be portable so that it can be transported to the patient.

Present large scale medical imaging systems include a patient table fixed in perpendicular relationship with the principle imaging plane of the imaging subsystem. A patient trauma table, such as the one described in U.S. patent application Ser. No. 08/193,562, filed Feb. 8, 1994 in the name of Gilbert W. McKenna and assigned to the present assignee, is advantageous because it is detachable from the imaging system to facilitate movement of the entire system through standard-sized room entryways, and can be useful in connection with power management and distribution in a medical imaging system.

U.S. Pat. No. 5,226,064 issued to Yahata et al. on Jul. 6, 1993 discloses a computerized tomographic scanning apparatus driven by rechargeable batteries. The batteries are adapted to store energy sufficient to execute a single scan or slice of a tomographic image consisting of a plurality of projections that together provide data for a two-dimensional image. In Yahata et al. a plurality of successive scanning cycles can be executed, each scanning cycle being of a duration of a minimum of about 20 seconds, and consisting of a scan phase of approximately 3 seconds, wherein the battery supplies power to an x-ray means, and a non-scanning phase of approximately 17 seconds, wherein the battery is recharged and power to the "low power consumption unit" is provided from the external source. Thus, during processing of the data relating to a complete tomographic image, the batteries of Yahata et al. must be recharged during the operation of the apparatus. In all of the embodiments described by Yahata et al. the "low power consumption unit" necessarily relies on the external power supply, whether the power is rectified or not. Thus, there is still a reliance on an external power supply and the concomitant vulnerability to power interruptions, anomalies, irregularities, disruptions and fluctuations. An electrical cable, or electrical slip rings, can be used to provide constant electrical contact between the external power source and the batteries. Yahata et al. is silent on any other method of providing such electrical contact.

OBJECTS OF THE INVENTION

It is a general object of the present invention to provide an apparatus for power management and distribution in a large scale medical imaging system of the type described that significantly reduces or substantially overcomes the problems of the prior art.

A more specific object of the present invention is to provide power to a rotating sub-system in a large scale medical imaging device without electrically contacting the rotating sub-system as it rotates.

A further object of the present invention is to allow the medical imaging sub-system to rotate at a predetermined speed for an extended period of time.

Another object of the present invention is to allow the medical imaging sub-system to rotate for a period of time sufficient to complete a medical imaging session, even if electrical power to the medical imaging system is interrupted during the medical imaging session.

Yet another object of the invention is to provide a large scale medical imaging system having higher product reliability in the presence of electrical power line anomalies, irregularities, and disruptions.

Still another object of the invention is to provide a medical imaging system that can operate using a broad range of external DC and AC power supplies, including a standard single phase AC electrical outlet.

And another object of the present invention is to provide a large scale medical imaging system powered by an uninterruptable power supply operable during the entire scanning process, including the time during which data is acquired and processed, independently of external power conditions.

And yet another object of the invention is to provide a medical imaging system that does not require additional power conditioning or power factor correcting equipment.

And still another object of the invention is to provide lower system weight and higher system portability.

And yet another object of the invention is to provide lower system power consumption.

And still another object of the invention is to avoid the use of slip rings, thereby avoiding the associated electrical noise, and other disadvantages associated with slip rings.

And yet a further object of the invention is to provide a medical imaging device that can operate using an unconditioned or poorly conditioned power line to power the device.

And still a further object of the present invention is to provide a tomographic scanning machine which is an improvement over the one described in U.S. Pat. No. 5,226,064.

Other objects of the present invention will in part be suggested and will in part appear hereinafter. The invention accordingly comprises the apparatus possessing the construction, combination of elements, and arrangement of parts, and the processes involving the several steps and the relation and order of one or more of such steps with respect to the others, all exemplified in the following detailed disclosure and the scope of the application, all of which will be indicated in the claims.

SUMMARY OF THE INVENTION

A large scale medical imaging system comprises an uninterruptable power supply for providing power to the system during the acquisition and processing of image data completely independent of external power conditions so as to operate independently of power fluctuations, disruptions and failures. The large scale medical imaging system preferably operates off of a regulated DC voltage, and the uninterruptable power supply is preferably in the form of batteries connected with respect to the external power source, and preferably the regulated DC voltage, so that the batteries are charging during normal conditions of the external power supply and instantaneously provide power when the external power falls below the threshold level provided by the batteries. The use of the uninterruptable power supply can be accomplished without the need for switching between the uninterruptable power supply and the external power supply.

In the preferred embodiment, the large scale medical imaging system includes means for correcting the power factor as measured from the external power line input of the system. In an alternative preferred embodiment, the means for correcting the power factor of the medical imaging system as measured from the line input of the large scale medical imaging system is cooperative with the uninterruptable power supply, and provides at least one regulated DC power signal.

In a preferred embodiment, the system is capable of operating off of a broad range of external power supplies, including DC voltage sources and single and three phase AC sources, and thus easily can be operated off of a standard $110^V$ AC single phase outlet, commonly found in homes or offices.

Another preferred embodiment includes an uninteruptable power supply means for use with a large scale medical imaging system, such as a CT scanner, having means for storing energy sufficient to acquire and process image data associated with at least an entire patient image.

The invention makes it possible for a medical imaging system, such as a CT scanner, PET scanner or an MRI imager, each of which require high peak power to perform medical imaging, to obtain power from a standard electrical outlet, such as a single phase, $110^V$ AC electrical outlet or a three phase AC electrical outlet. This is accomplished in part by storing electrical power using an energy storage device, such as a plurality of rechargeable batteries.

A preferred embodiment of the apparatus of the invention reduces power consumption by incorporating corrector means for correcting the power factor of the medical imaging system as measured from the line input of the medical imaging system. In another preferred embodiment, the invention includes DC/DC converter means for providing a plurality of regulated DC power signals, each regulated DC power signal being provided at one of a plurality of DC voltages.

Both the power factor corrector and the DC/DC converter are protected against a variety of over-current, over-power, over-voltage, under-voltage, and over-temperature conditions.

In another preferred embodiment, the invention includes a data processor for allocating power between at least the means for receiving and storing energy and the data processor, and optionally at least one motor controller.

BRIEF DESCRIPTION OF THE DRAWINGS

The invention will be more fully understood from the following detailed description, in conjunction with the accompanying figures, wherein.

DETAILED DESCRIPTION OF THE DRAWINGS

The power management and distribution system in accordance with the present invention is preferably described in conjunction with a large scale medical imaging system in the form of a CT scanner system. In particular, the invention will be discussed in the context of a CT scanner system having a variety of components that require power to operate. A CT scanner system, or any other large scale medical imaging device that incorporates the power management and distribution system of the invention, may include components not herein specifically mentioned, or may omit components herein specifically mentioned. Nevertheless, the invention will be useful in a wide variety of large scale medical imaging systems such as magnetic resonance imaging (MRI) systems and positron emission tomography (PET) systems, and is not limited to the example herein described.

Figure 1:
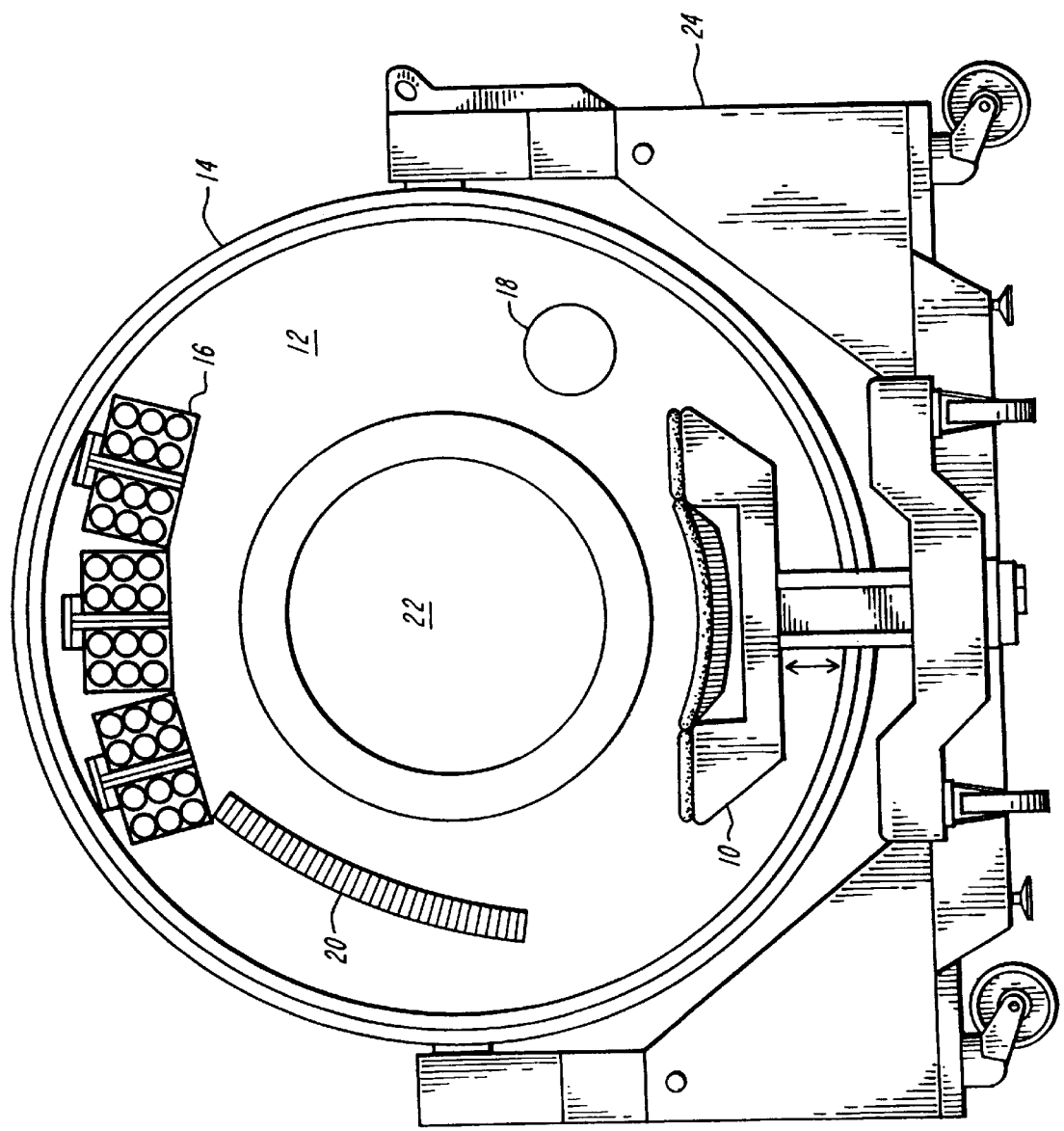
FIG. 1 is a plan view of a representative computed tomography (CT) scanner system that can incorporate the power management and distribution system of the present invention.

Referring to FIG. 1, a patient table 10 is shown that has variable height and longitudinal extension. The preferred patient table is described in greater detail in copending U.S. patent application Ser. No. 08/193,782 filed Feb. 8, 1994 in the name of Gilbert W. McKenna, and assigned to the present assignee (Attorney's Docket No. ANA-58). The table supports a patient (not shown) to be scanned. The scanner system also includes a disk 12 rotatably supported in an annular frame 14 and supporting a battery assembly 16, and further includes an X-ray source assembly 18. The illustrated CT scanner system is of the third generation type, and therefore also includes a detector array 20 positioned on disk 12 diametrically across from the X-ray source assembly 18. The X-ray source assembly 18 and detector array 20, which generally form the components for generating image data, rotate with disk 12 about the rotation center of the disk. In addition, components in the form of a data acquisition system (not shown in FIG. 1 but represented by DAS 114 in FIG. 2B) are mounted on disk 12 for acquiring the image data from detector array 20. Disk 12 is provided with a round center aperture or opening 22 that is sized and disposed so as to accept the patient during a CT scan in which the X-ray source 18 and detector array 20 rotate about the portion of the patient positioned in opening 22 and generate image data representing a cross-sectional image through the portion of the patient positioned in opening 22, as is well known. A cart 24 is also provided for movably supporting the annular frame 14 and for cooperating with patient table 10.

The CT scanner system includes a variety of components that either function as power storage devices or require power to operate. In the preferred embodiment, these components are provided on all three of the major elements of the CT scanner system, i.e., patient table 10, disk 12 and cart 24. For example, data is preferably transferred between disk 12 and cart 24 through an RF link (not shown), such as the RF link system described in copending application, U.S. Ser. No. 08/174,664, filed in the names of Bernard M. Gordon, Richard B. Johnson, Iosef Izrailit, Hans Weedon, and Douglas Abraham, on Dec. 27, 1993, and assigned to the present assignee (Attorney's Docket No. ANA-29). The RF link is also used to control power to disk 12 for operating the X-ray source assembly 18 and for powering the various components that acquire data from each scan. Accordingly, a power management and distribution system is needed to meet the power requirements of the CT scanner system.

Figure 2A:
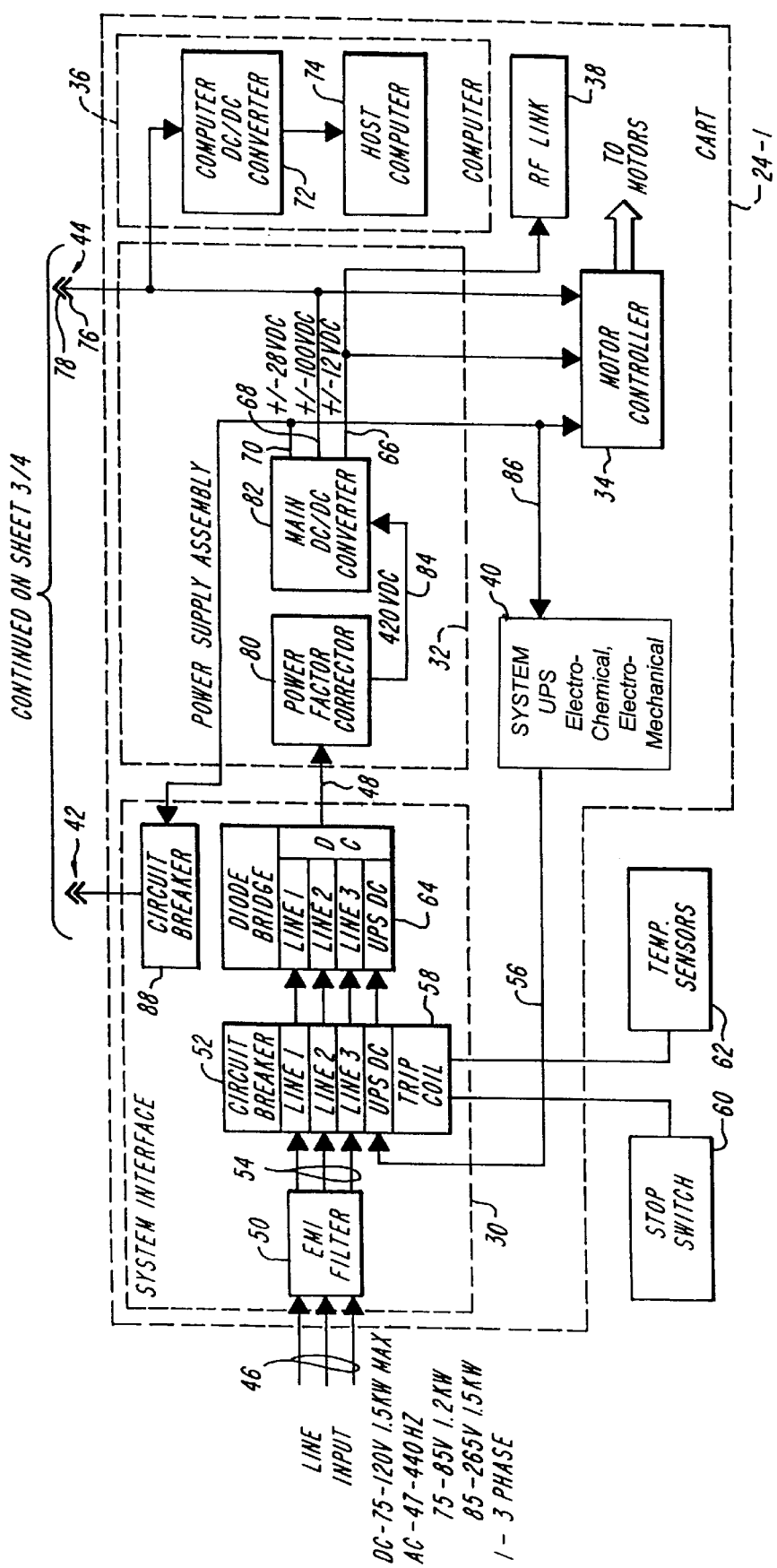
FIG. 2A is a block diagram of a preferred embodiment of the power management and distribution system of the present invention.
Figure 2B:
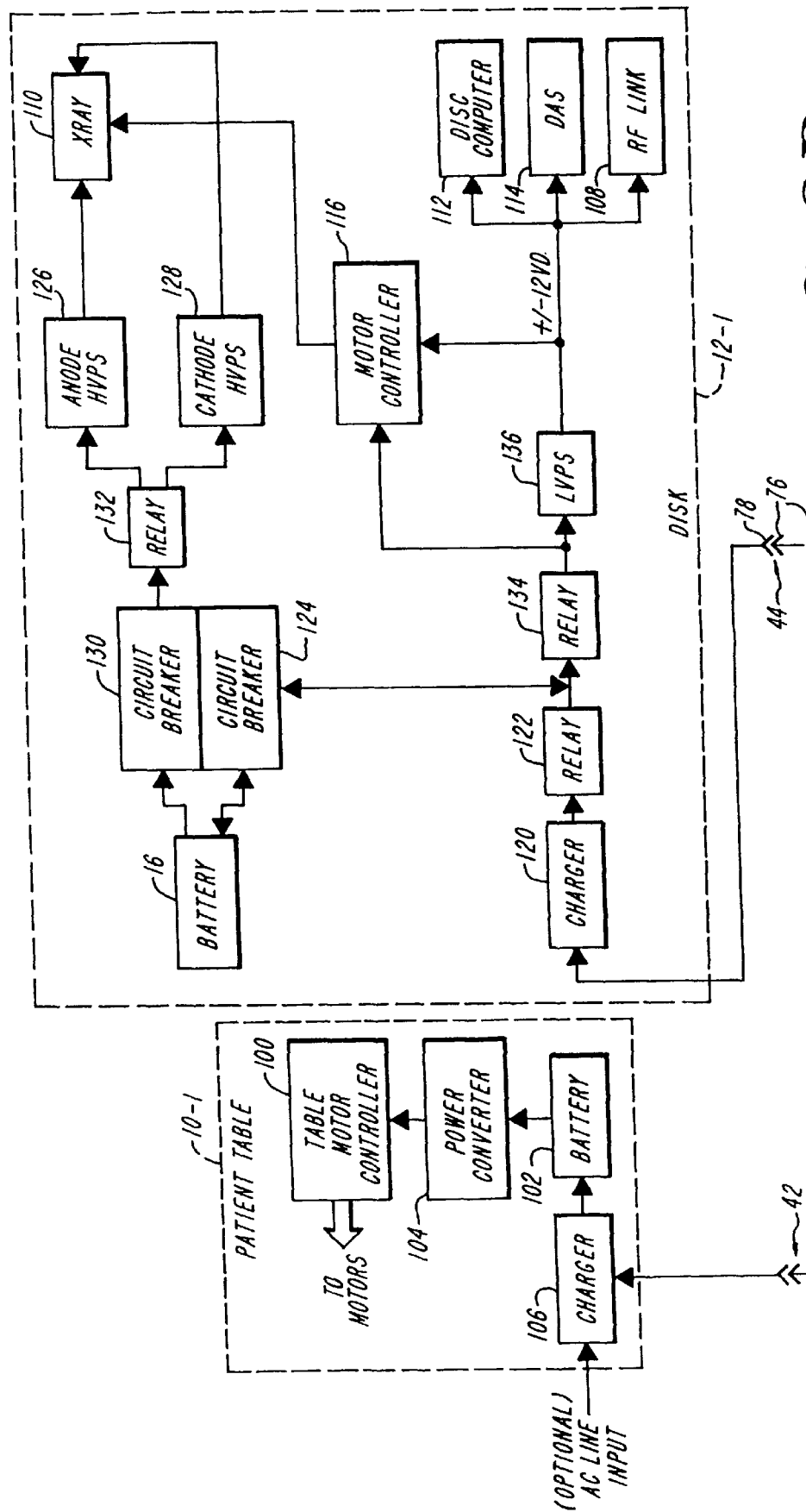
FIG. 2B is a block diagram illustrating a preferred configuration for the patient table and rotatable disk of FIG. 1.

Referring to FIGS. 2A and 2B, the subsystems that generate power supplied to the components configured in patient table 10, disk 12 and cart 24 are shown in detail. In FIG. 2A, a system interface 30 is combined with a power supply assembly 32 for generating a group of DC signals through appropriate connections to a motor controller 34, cart computer 36, and RF link 38. An uninterruptable power supply (UPS) configured as system UPS 40 is included to provide a source of uninterruptable power to system interface 30. A subset of the DC signal group from power supply assembly 32 is supplied via connector 42 and connector 44 to the subsystems located on patient table 10 and disk 12 (discussed infra in connection with FIG. 2B). The components and subsystems enclosed by the outermost block in FIG. 2A are integrated into a cart module 24-1 located in cart 24, except for the static portion of the RF link (represented by RF link 38) which may be supported by frame 14.

As module 24-1 indicates, cart 24 supports cart computer 36 for at least controlling the power through the RF link to X-ray source 18, and for controlling the components for processing data received from disk 12 that is generated by the data acquisition system, indicated at 114 in FIG. 2B, positioned on disk 12. In addition, power is required to operate the static portion of the RF link 38. Power is also provided to motor controller 34 for controlling a plurality of associated motors (not shown) that serve to rotate disk 12 within frame 14, and to move frame 14 and disk 12 for tilting and translation. A more detailed description of such a tilting and translation system is described in copending application U.S. Ser. No. 08/193,562, filed in the name(s) of Gilbert W. McKenna on Feb. 8, 1994 and assigned to the present assignee (Attorney's Docket No. ANA-37).

In accordance with one aspect of the present invention, the CT system can be operated using a broad range of external power sources including both conditioned and unconditioned power sources, both DC and AC voltages, and, in the case of the latter, single-phase and three-phase over a broad range of frequencies. Thus, the system can be powered from a standard, unconditioned single phase AC voltage source provided at a wall outlet. Accordingly, system interface 30 is adapted to accept a line input 46 covering a broad range of AC voltages, frequencies, and power levels, and is further adapted to interface with DC and single or three phase AC electrical outlets. For example, a preferred embodiment of the invention accepts AC voltages from 75 V to 85 V at 1.2 KW and 85 V to 265 V at 1.5 KW, AC frequencies from 47 Hz to 440 Hz (with a total harmonic distortion (THD) of less than 10%), and DC voltages of from 75 to 120 VDC, 1.5 KW MAX. Input currents can be as high as 20 Amps DC, and 20 Amps RMS AC. Thus, the invention allows a medical imaging device to operate using standard electrical outlets in a variety of countries, including the industrialized countries of the United States, Japan, and the western European nations, as well as outlets found in military environments and second, third and fourth world countries.

In an alternate embodiment of the invention, power is provided as a function of input line conditions as follows:

TABLE 1

| INPUT VOLTAGE | POWER DELIVERED |
| --- | --- |
| 40 to 75 VDC | 600 Watts |
| 75 to 80 VDC | 1000 Watts |
| 80 to 90 VDC | 1300 Watts |
| 90 to 350 VDC | 1500 Watts |
| 75 to 85 VAC | 1000 Watts |
| 85 to 100 VAC | 1300 Watts |
| 100 to 290 VAC | 1500 Watts |

Regardless of the line input specifications, system interface 30 provides a DC output 48. In particular, when the line input 46 is AC, the DC output 48 is pulsating DC. Alternatively, when the line input 46 is DC, the DC output 48 is direct DC.

Referring to system interface 30, an electromagnetic interference (EMI) filter 50 is provided that substantially prevents frequencies generated by the RF link 38 and cart computer 36 from being broadcast over the line input 46, thereby promoting compliance with Federal Communications Commission regulations relating to electromagnetic interference from electrical devices. The EMI filter 50 also substantially prevents local electromagnetic interference from affecting the apparatus of the invention.

System interface 30 also includes a circuit breaker 52 having four poles that trip on an over-current condition to protect the apparatus of the invention from excessive electrical currents. For example, if the current through any one of the four poles exceeds 20 amperes, for example, the entire breaker 52 will trip. Three of the four poles are dedicated to three lines 54 from EMI filter 50 that can carry the three phases of a three-phase line, or one of the three lines can carry a single phase. The fourth pole is for a UPS line 56 that provides power from system UPS 40 to system interface 30 in the event of a power failure, fluctuations, or distortions of the line input 46.

Circuit breaker 52 also includes a "trip coil" 58 for causing breaker 52 to interrupt current flow therethrough upon actuation by a user of an emergency stop switch 60, or upon detection by one or more thermal sensors 62 (approximately positioned on or near the cart 24, disk 12, and/or table 10) of a temperature above a predetermined threshold temperature. In a preferred embodiment, it is sufficient that circuit breaker 52 be DC rated, although an AC rated circuit breaker could also be used.

System interface 30 further includes a diode bridge 64, connected to the output of circuit breaker 52, that rectifies one-, two-, or three-phase alternating current (AC), as provided by the line input 46, to supply pulsating direct current (DC). Diode bridge 64 is preferably a standard three-phase bridge rectifier rated at 600 V and 25 A, such as one manufactured by International Rectifier. In the case that line input 46 is DC current, diode bridge 64 provides straight DC current, i.e., DC current without a ripple current component. The DC signal from diode bridge 64 appears as power output 48.

The power supply assembly 32 receives power output 48 from system interface 30, and provides power via a plurality of DC signals (i.e., on lines 66, 68 and 70) at a variety of DC voltages (e.g., ±12 VDC, ±100 VDC, and ±28 VDC, respectively) to the cart motor controller 34, frame RF link 38, system UPS 40, and cart computer 36. Power is coupled from power supply assembly 32 over line 68 to a computer DC/DC converter 72 within cart computer 36, which is further linked to a host computer 74. The power supply assembly 32 also provides power over line 68 (via connector 44) to the rotatable disk 12 when the disk 12 is parked in a charging position. In particular, to allow power transfer from the power supply assembly 32 to a battery charger located on disk 12 (discussed infra in connection with FIG. 2B), power connector 44 includes a frame portion 76 interfaced with the power supply assembly 32 and electrically connected to a scanner portion 78 that is coupled to the battery charger.

In accordance with another object of the present invention, the power supply assembly 32 also includes a power factor corrector 80 in order to correct for the power inefficiencies created by the input impedance of the system. The power assembly 32 also includes a main DC/DC converter 82 for converting a DC voltage input to a plurality of DC output signals at various DC levels. Power factor corrector 80 converts the power provided by diode bridge 64 on line 48 to the high voltage DC power 84 required to drive the main DC/DC converter 82, while maintaining unity power factor as seen at the line input 46. For example, the high voltage DC power 84 is preferably provided at 420 ±2 VDC non-isolated, having a ripple voltage that is less than 10V peak-to-peak at 50 Hz, 1500 Watts load. The power factor corrector 80 can operate using input voltages of from 80 to 350 VDC or from 75 to 290 VAC over a frequency range of 47 to 440 Hz.

Power factor corrector 80 is preferably a boost voltage regulator using a power factor controller integrated circuit from Micro Linear (ML 4812) and power MOSFETS from Advanced Power Technology (APT6030). For more information on the design of circuits using these components, it is useful to refer to the data sheets and application notes available from the manufacturer, herein incorporated by reference, and to refer to commonly available reference books, such as *Switching Power Supply Design* by A. I. Pressman, herein incorporated by reference.

In a preferred embodiment, power factor corrector 80 is adapted to ensure that the maximum current drawn from the line input 46 is 19 amperes, including inrush current, regardless of whether the input is AC or DC, and regardless of the voltage level. The power factor of power factor corrector 80 is maintained at greater than 99% for the lower voltages (e.g., 75 to 140 VAC) of a single phase AC input, and greater than 97% at the higher voltages (e.g., 150 to 290 VAC). The power factor corrector 80 preferably maintains greater than 94% overall efficiency over all operating conditions.

By way of background, the power factor of a single-phase circuit is the cosine of the phase angle between the current and the voltage sinusoids. Consequently, if the current and voltage are in quadrature (phase angle is 90 degrees), the power factor is zero, and no power is transferred to the circuit, i.e., the circuit is purely reactive. If the current and voltage are substantially in phase (phase angle is zero), power is transferred with the highest efficiency, i.e., the circuit is purely resistive. A power factor between zero and one (or between 0% and 100%) indicates a combination of reactive and resistive behavior. Also, the power factor of a balanced three-phase system, when the waveforms of voltage and current are sinusoidal, is defined as the cosine of the angle between phase voltage and phase current.

The power factor is important because power companies typically charge non-residential users according to the power factor, since even though reactive currents do not result in useful power being delivered to a load, they cost the power company a significant amount due to $I^2R$ heating losses in the resistance of generators, transformers and wiring, for example. Thus, inclusion of the power factor corrector 80 serves to cancel the reactance of the circuitry of the medical imaging system that incorporates the invention, thereby improving the efficiency with which electrical energy is utilized, with a consequent reduction in the cost of operating the medical imaging system. Further, inclusion of the power factor corrector 80 eliminates the need to purchase an external power factor corrector for use with the medical imaging system, thereby further reducing the cost of operating the large scale medical imaging system. Note, therefore, that the power factor corrector 80 can be connected at other places in the system, e.g., directly to the line input 46, or between EMI filter 50 and circuit breaker 52, or between circuit breaker 52 and diode bridge rectifier 64.

Referring to the main DC/DC converter 82, the high voltage DC power output 84 provided by power factor corrector 80 is converted by the main DC/DC converter 82 to the plurality of voltages (i.e., the signals appearing on lines 66, 68, and 70) used to operate the various sub-systems of the medical imaging system. For example, in a preferred embodiment, the frame RF link 38 uses a low voltage from line 66, such as ±12 VDC to within ±1.0 VDC at 16 amperes maximum (ripple less than 50 mv p-p below 20 MHz), and the cart computer 36 and the battery charger on rotatable disk 12 coupled to connector 44 use a high voltage from line 68, such as +/−100 VDC to within ±0.5 VDC at 7 amperes maximum (ripple less than 50 mv p-p below 20 MHz). An intermediate voltage, such as ±28 VDC to within ±2 VDC at 10 amperes maximum (ripple less than 50 mv p-p below 20 MHz), is delivered to system UPS 40 via line 86, and to a table battery charger via port 42 (discussed infra in connection with FIG. 2B). The components connected to port 42 are protected against adverse line conditions or signal levels on line 70 by a circuit breaker 88 coupled between line 70 and port 42. The cart motor controller 34 uses each of the available voltages from the main DC/DC converter 82.

During extended input line conditions, the DC/DC converter 82 will continue to provide the listed outputs, but not necessarily with load and input regulation of 1% or less.

In accordance with another aspect of the present invention, the CT scanner system includes the aforementioned system uninterruptable power supply (UPS) 40 for providing the necessary power to all of the components for the entire CT scanner operation in the event of disruptions, distortions, fluctuations, or failure in the external power supply, regardless of the nature of the problem, e.g., whether the problem is reduced levels of power (such as encountered in a brown out), total power failure (such as encountered during a black out), failure during a particular phase or phases of each cycle of the AC voltage, whether intentional (where the AC input voltage is rectified) or unintentional, etc. This ensures that a scan will always be completed regardless of any problem with respect to a drop in power from the external power supply that arises during the operation of the CT scanner.

The UPS 40 is preferably in the form of a bank of batteries, connected together to provide sufficient energy, e.g., 600 to 700 watts at 40 to 48$^V$ DC , to perform at least one entire scan, including the acquisition and processing of the image data. While the preferred UPS 40 is a bank of batteries, the system UPS can take other forms of energy storage devices, such as electromechanical energy storage devices (e.g., rotating disks of large mass connected to a generator), or electrochemical devices such as thermal storage devices (e.g., exothermal devices for releasing heat which in turn can be used to heat water for driving a generator, etc.). The system UPS 40 is preferably provided as part of the cart module 24-1. Preferably, the UPS 40 is connected to the power supply assembly 32 via line 86 so that energy is stored in the UPS 40 during normal operating conditions of the external power supply. The UPS 40 is also connected to an input of circuit breaker 52 in system interface 30 (via line 56) that is separate from the inputs receiving the power from the external power supply source. The power from UPS 40 is provided through system interface 30 (i.e., through lines "UPS DC") to the power supply assembly 32 independently of the external power (which flows through "LINE 1", "LINE 2", "LINE 3") so that both sources are simultaneously provided to the input of the power supply assembly 32 without any switching. As long as the external power is adequate for operating the CT scanner, the UPS 40 will remain fully charged. However, should the external power levels (in this case the voltage levels) drop below the level provided by the UPS 40, power from the UPS 40 will be instantaneously available to the power supply assembly 32 (since no switching is necessary).

The UPS 40 is preferably energized by the main DC/DC converter 82 of the power supply assembly 32, which is connected to the UPS 40 through the power supply line 86 so that the stored energy is preferably derived from the external power source.

Referring to FIG. 2B, which shows an implementation for patient table 10 and disk 12 that receives and uses the power generated by the subsystems of FIG. 2A, a patient module 10-1 includes components integrated on patient table 10 and is adapted to receive an optional AC line input and power signals from power supply assembly 32 via port 42. Also shown by FIG. 2B is a disk module 12-1 that includes components integrated on disk 12 and that is adapted to receive power signals from power supply assembly 32 via the scanner portion 78 of connector 44.

Patient module 10-1 includes a table motor controller 100 for controlling motors (not shown) that raise and lower the patient, and optionally for controlling motors (not shown) that laterally translate the recumbent patient into opening 22 of disk 12. Motor controller 100 and the associated motors require electrical power, which they obtain from a battery 102 via a power converter 104. Battery 102 is charged by a charger 106 that receives power from the power supply assembly 32 via power supply port 42, or optionally receives power from a standard electrical outlet via an AC line input.

Referring to the disk module 12-1, the rotatable disk 12 supports a rotatable portion of the RF link (represented by RF link 108) for transferring data to and from the cart computer 36. The disk module 12-1 also supports an X-ray source assembly 110, a disk computer 112, a data acquisition system (DAS) 114, and a motor controller 116 for controlling motors (not shown) in the X-ray source assembly 110, such as the motor for rotating the anode of the X-ray tube.

The disk module 12-1 further includes energy storage means, such as battery 16 that is charged by a charger 120 via a relay 122 (to provide electrical isolation), and a circuit breaker 124. Battery 16 provides power to an anode high voltage power supply 126 and a cathode high voltage power supply 128 via a circuit breaker 130 and a relay 132. The anode high voltage power supply 126 and the cathode high voltage power supply 128 provide power to the anode and cathode of the X-ray tube assembly 110. Also, the motor controller 116 provides power to motors within the X-ray tube assembly 110. The motor controller 116 receives power from charger 120 through relays 122 and 134, and from battery 16 via circuit breaker 124 and relay 134. The motor controller 116 also receives power from a low voltage power supply 136 that provides a low voltage (e.g., ±12 VDC).

Additionally, the disk computer 112, the data acquisition system (DAS) 114, and the scanner RF link 108 receive power from the low voltage power supply 136.

Figure 3:
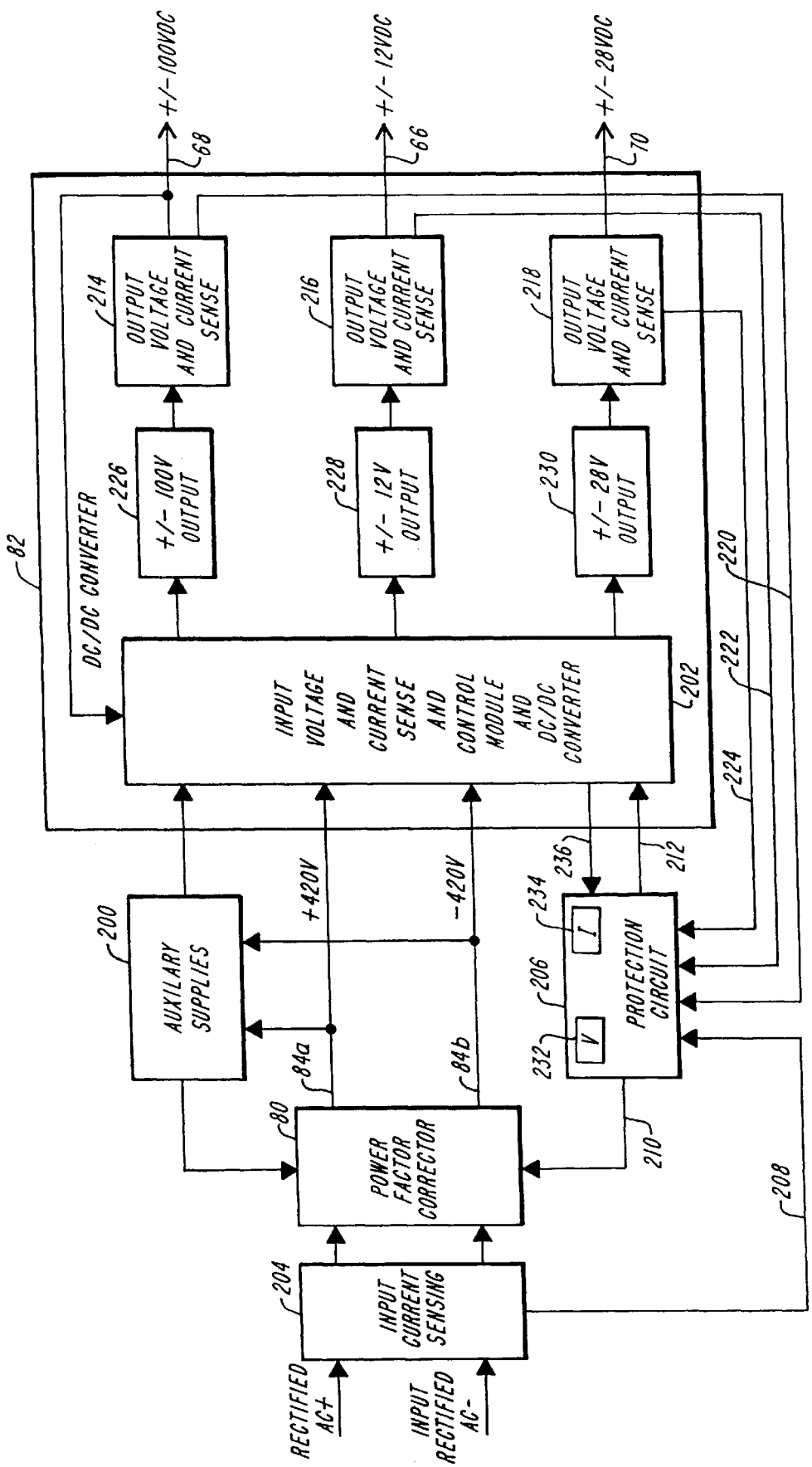
FIG. 3 is a block diagram depicting a preferred implementation of the power factor corrector and main DC/DC converter of FIG. 2A.

Referring to FIG. 3, which illustrates the integration of power factor corrector 80 with the main DC/DC converter 82, auxiliary supplies 200 are provided to supply power to control circuitry (not shown) within power factor corrector 80, and to supply power to control circuitry within an input voltage and current sense and control (IVCSC) and DC/DC converter module 202 of DC/DC converter 82. Each auxiliary supply is preferably a forward switching converter that provides ±15 VDC and +5 VDC to supply the controller and protection circuitry of the power factor corrector 80 and the DC/DC converter 82. It receives its power from the +420 VDC output 84a and −420 VDC output 84b of power factor corrector 80. During start-up and fault conditions, these outputs 84a and 84b are each a rectified input voltage to the auxiliary supplies 200, whose outputs are passed through an inductor in the power factor corrector 80 with no amplification. In all cases, the auxiliary supplies 200 will be ON in the presence of a voltage on its inputs.

An input current sensing module 204 is preferably provided at the input of power supply assembly 32 (i.e., at the input of power factor corrector 80) for sensing the input current delivered to the power factor corrector 80, and for generating a control signal that instructs a protection circuit 206 to disable power factor corrector 80 and DC/DC converter 82 when the current on input line 46 exceeds a current threshold.

More particularly, the power factor corrector 80 also functions to limit the current drawn from the line input 46 regardless of its load and input voltage, e.g. 19 amperes. As noted above, the input current sensing module 204 senses the input current delivered to the power factor corrector 80, and provides a current measurement signal 208 to the protection circuit 206. If the current drawn from line input 46 (of FIG. 2A) exceeds a current threshold, such as 18 amperes, the protection circuit 206 disables the power factor corrector 80 and the DC/DC converter 82 by deasserting the enable lines 210 and 212, respectively, thereby shutting down the medical imaging system. Thus, power for a medical imaging system that incorporates the power distribution and management system of the invention can be supplied by a standard wall outlet.

The IVCSC module 202 provides over-power protection by measuring the current and multiplying the measured current by the known voltage provided by the power factor corrector 80 to obtain the power level. Thus, if current exceeds a threshold determined in part by the regulated voltage provided by the power factor corrector 80, both the corrector 80 and the converter 82 are immediately shut down by the protection circuit 206, disabling an enable of the switching converter within both the power factor corrector 80 and the DC/DC converter 82.

Detection circuits are provided within the IVCSC module 202, the input current sensing module 204, and the output voltage and current sense modules 214, 216, and 218. These detection circuits compare voltages measured at their respective inputs to minimum and maximum acceptable threshold voltages. The outputs of these modules (i.e., output signals 220, 222, and 224 from modules 214, 216, and 218, respectively) are provided to the protection circuit 206, wherein the outputs represent the relationship of the respective output voltage to a corresponding voltage threshold. Each output can take the form of a binary signal that indicates either compliance or non-compliance with the voltage condition defined by a minimum and maximum voltage threshold. Moreover, each sense module receives an input from a respective DC output module, i.e., sense modules 214, 216, and 218 receive inputs from ±100V output module 226, ±12V output module 228, and ±28V output module 230, respectively.

More specifically, protection circuit 206 includes both voltage protection circuitry 232 and current protection circuitry 234 that can take any form known to one skilled in the art that provides the following functionality. If any voltage sense module, such as the modules 202, 214, 216, and 218, detects a voltage that is out of an allowed voltage range, the module will promptly disable the power factor corrector 80 and DC/DC converter 82. The current protection circuitry 234 starts a timer upon receiving a signal from a current sense module, such as 202, 214, 216, or 218, which indicates that a measured current has exceeded an allowed current threshold. If the current-fault condition is still present after a pre-set delay period, such as 200 milliseconds, the enables of the power factor corrector 80 and the DC/DC converter 82 are disabled. Further, if a current fault occurs, the current protection circuitry 234 latches to prevent a re-enabling of the power factor corrector 80 and the DC/DC converter 82 until latch circuitry of the current protection circuitry 234 is reset.

The use of a delay feature in the current protection circuitry 234 permits momentary power surges to occur that are above the normal maximums. These power surges are not harmful to the circuitry of the medical imaging system or input power line, due to their limited time duration. Note that drawing excessive current, to the point of being harmful, should be accompanied by a voltage fault. The time delay feature permits the medical imaging system to operate closer to the limits of the power available from a standard line without having to shed excessive loads so as to provide the current handling capacity needed to handle the peak currents that occur when energizing the various subsystems of the medical imaging system. The time delay feature also permits the power supply assembly 32 to start faster when it is first turned on.

The delay feature in the current protection circuitry 234 can be implemented in a variety of ways that are well known to one skilled in the art. For example, the delay feature circuitry may be implemented using any of the following elements: R-C delay circuits, mechanical timers, analog delay lines, digital delay lines, digital timers, or other means for introducing a time delay between receiving a signal indicating an overcurrent condition and providing a disable signal to enable means within the power factor corrector 80 and DC/DC converter 82.

The foregoing description will be more clearly understood from the following discussion of the operation of the system. Referring to FIGS. 2A–B and 3, system interface 30 receives a signal on line input 46 and delivers a DC output 48. In particular, referring first to FIG. 2A, when the line input 46 is AC, the DC output 48 is pulsating DC, and when the line input 46 is DC, the DC output 48 is direct DC. When voltage is applied (via output 48) at the input to power supply assembly 32, a rectifier bridge (not shown) within the auxiliary supplies (of FIG. 3) 200 rectifies the input voltage. The rectified input voltage causes the auxiliary supplies 200 to activate when the rectified voltage is greater than a pre-set brown-out threshold, such as a 70 V peak. The auxiliary supplies 200 then supply power to the controllers of the power factor corrector 80 and the DC/DC converter 82, which then together provide the regulated voltages 66, 68, and 70.

Referring specifically to the operation of the power factor corrector 80, upon start-up, as soon as the rectified input voltage exceeds the pre-set brown-out threshold, the ML 4812 controller chip within power factor corrector 80 will start to switch the MOSFETS ON and OFF at a rate of 100 KHz using a pulse width modulation (PWM) technique. When the MOSFETS are turned ON, the current through the storage inductors of the ML 4812 is increased linearly. When the MOSFETS are turned OFF, all energy stored in the inductors is delivered to the output capacitors so as to establish the ±420 VDC at the output of the power factor corrector 80. On a cycle-by-cycle basis, the power factor corrector circuitry limits the ON-time of the MOSFETS as needed to maintain the output voltage at ±420 VDC. When the power factor corrector 80 has no loads, the output voltages will build up to ±435 VDC, at which time the built-in over-voltage protection circuitry will cause the ML 4812 controller to shut down its output and turn the MOSFETS OFF until the output voltages drop below ±420 VDC. There is an internal bleeder resistor that discharges this output in the absence of a load.

The DC/DC converter 82 (of FIGS. 2A and 3) receives power over lines 84$a$ and 84$b$ at +/−420 VDC from power factor corrector 80 and converts the power on these lines into isolated voltages 66, 68, and 70. The DC/DC converter 82 preferably operates as an H-bridge forward converter. The phase modulation is controlled using well known circuitry, such as an ML 4818 integrated circuit from Micro Linear.

The DC/DC converter 82 is protected against over-voltage, under-voltage, over-current, and over-temperature at each output, and against excessive power consumption at the input to converter 82. For any DC/DC converter fault that occurs, except over-current and excessive power, both the converter 82 and power factor corrector 80 are disabled by the protection circuit 206 of FIG. 3. If an over-voltage condition is detected, the corrector 80 and converter 82 are promptly shut down. Over-temperature conditions are detected within the protection circuit 206 by connection with one or more thermal switches (not shown), preferably mounted near the heat sinks of the MOSFETs of converter 82 and power factor corrector 80.

Upon detecting either an over-current or a total-power fault condition, the corrector 80 and converter 82 will be shut down after a delay period, such as 200 milliseconds. The delay period is included so as to distinguish between shorted outputs and initial power-up when the output capacitors are empty. Also, the delay period permits system functions, such as motor operation, to momentarily exceed normal operating limits without shutting the system down. Further, the delay period ensures that the power supply assembly 32 will not be damaged due to sudden shorted outputs during operation or power-up with a shorted output.

Referring specifically to FIG. 3, operation of the main DC/DC converter 82 requires that the enable signal 212 be asserted by protection circuit 206. Thus, converter 82 can be shut down by deasserting the enable signal 212. To limit the power drawn from the line input 46 (shown in FIG. 2A) to a pre-set maximum power limit, which depends on the line input voltage of line input 46, the main DC/DC converter 82 is cooperative with the protection circuit 206. In particular, the input voltage and current sense and control (IVCSC) module 202 within the DC/DC converter 82 measures the current at the output of the power factor corrector 80. The IVCSC module 202 provides a current measurement signal 236 to the protection circuit 206. Upon detecting a current level and line input voltage that indicates that the pre-set maximum power limit has been exceeded, the protection circuit 206 deasserts the enable line 212 required by the DC/DC converter 82 to operate. Consequently, the DC/DC converter 82 will shut down, thereby halting the supply of power via the output power lines 66, 68, and 70.

For example, when the line input voltage is between 75 VAC and 85 VAC, the pre-set maximum power limit is 1000 VA; when the line input voltage is between 85$^V$ AC and 100$^V$ AC, the pre-set maximum power limit is 1300 VA; and when the line input voltage is between 100$^V$ AC and 290$^V$ AC, the pre-set maximum power limit is 1500 VA.

In addition, the maximum level of power can be delivered only if the current limit of each of the outputs 66, 68, and 70 of DC/DC converter 82 is not exceeded. The current limit of each of the outputs 66, 68, 70 is measured by the output voltage and current sense modules 216, 214 and 218, respectively, of DC/DC converter 82. Each output voltage and current sense module 214, 216, 218 provides to the protection circuit 206 a corresponding output current measurement signal 220, 222 and 224, respectively, which is representative of the output current of a respective output module 226, 228 and 230 of the DC/DC converter 82. When these current limits are not exceeded, the main DC/DC converter 82 maintains at least 95% efficiency.

However, if the current limit of any one of the outputs 66, 68, and 70 is exceeded for more than an acceptable delay period, such as 200 milliseconds, the enable signal 212 is deasserted by the protection circuit 206, thereby disabling the converter 82 and reducing all output voltages 66, 68, 70, and consequently disabling the medical imaging system.

In summary, if the power drawn by the medical imaging system exceeds the pre-set power limit for a particular voltage, or if the current limit of any of the outputs 66, 68, and 70 is exceeded, all output voltages will be reduced, and the converter 82 will shut down the medical imaging system within 200 milliseconds.

Moreover, if any output 66, 68, or 70 is shorted, or drifts more than 10% from its nominal voltage, as detected by a respective output voltage and current sense module 214, 216, 218, the system will be promptly shut down by the protection circuit 206. Thus, the power system of the invention is fully protected from under-voltage, over-voltage, over-current. The power system is also protected against an over-operating-temperature condition, as discussed above.

Referring to FIG. 2A, as noted above, the power signals from UPS 40 and the external power sources are independently provided through system interface 30, allowing the signals from both sources to be simultaneously available to the input of power supply assembly 32 without any switching. Accordingly, if the signal levels from the external power sources fall below the level provided by UPS 40, power from UPS 40 will be instantaneously available to the power supply assembly 32 (since no switching is necessary). Otherwise, UPS 40 will remain fully charged as long as the external power is sufficient to operate the CT scanner.

Referring again to FIG. 2A, the host computer 74 performs load management by apportioning available power from the power line 46 according to particular system functions to be performed. Certain functions are of higher priority than other functions, and therefore are last to be deprived of power. Examples of high priority functions include operation of the cart computer 36 and the cart RF link 38. However, since the battery 16 (see FIG. 2B) is charged over an extended period or periods of time, the particular time that the battery 16 is charged is not critical. Consequently, charging of the battery 16 is a lower priority than most other system functions. Thus, the rate that the charger 120 provides energy to the battery 16 on board the rotating disk 12 is partly determined by the power required by other system components (e.g., an electric motor controlled by the motor controller 34) and their priority relative to the priority of the battery 16. Some functions are postponable, and can therefore have power use interrupted, such as certain motor functions, including raising and translating the patient table. Thus, when an electric motor requires power, the power provided to the charger 120 is reduced.

The system thus described provides for an improved apparatus for power management and distribution in a large scale medical imaging system, such as a CT scanner, that significantly reduces or substantially overcomes the problems of the prior art. The system provides power to a rotating sub-system in a large scale medical imaging device without electrically contacting the rotating sub-system as it rotates. The medical imaging sub-system is allowed to rotate at a predetermined speed for an extended period of time as a function of the charge provided from an uninterruptable power supply. The medical imaging sub-system is thus allowed to rotate for a period of time sufficient to complete a medical imaging session, even if electrical power to the medical imaging system is interrupted during the medical imaging session. The system provides for higher product reliability in the presence of electrical power line anomalies, irregularities, and disruptions. The medical imaging system can operate using a standard single phase 110$^V$ electrical outlet. In addition, UPS 40 insures that a scan will be uninterrupted and completed even in the event of loss of external power during the scan. The power supply includes a power factor corrector for more efficient power usage and lower power consumption. The system is relatively light weight portable system. The system avoids the use of slip rings, thereby avoiding the associated electrical noise, and other disadvantages associated with slip rings. The CT scanner can operate using an unconditioned or poorly conditioned power line to power the device. The CT scanner is an improvement over the tomographic scanner described in U.S. Pat. No. 5,226,064.

Other modifications and implementations will occur to those skilled in the art without departing from the spirit and the scope of the invention as claimed. Accordingly, the above description is not intended to limit the invention except as indicated in the following claims.

What is claimed is:

1. A computed tomography imaging apparatus comprising a disk for rotatably supporting an x-ray source and x-ray detection means for use in generating a scanned image during a scanning operation, the apparatus further comprising:

uninterruptible power supply means for storing at least sufficient energy for operating said apparatus through an entire scanning operation;

power supply assembly means for providing power to the apparatus;

means for receiving electrical power from an external power source so as to simultaneously apply electrical power to said apparatus during a scanning operation and to said uninterruptible power supply means; and means for applying power stored in said uninterruptible power supply means to said means for receiving said electrical power from an external power source so that said apparatus utilizes external power from said external power source when said external power is sufficient to operate said apparatus during a scanning operation, and immediately utilizes power from said uninterruptible power supply means when said external power is insufficient to operate said apparatus so as to provide uninterrupted operation of said apparatus through the entire imaging operation.

2. Apparatus according to claim 1, wherein said uninterruptible power supply means includes an electro-chemical system for storing energy.

3. Apparatus according to claim 1, wherein said uninterruptible power supply means includes an electromechanical system for storing energy.

4. Apparatus according to claim 1, wherein said uninterruptible power supply means includes a battery system for storing energy.

5. Apparatus according to claim 4, wherein said apparatus further includes means for charging said battery system with at least some of said external power so that said battery system can be charged when sufficient external power is provided to said means for receiving electrical power from an external power source.

6. Apparatus according to claim 1, further including means for generating at least one regulated DC power signal, in response to power received by said means for receiving electrical power from an external power source, for operating said apparatus.

7. Apparatus according to claim 6, wherein said means for generating at least one regulated DC power signal generates at least one other regulated DC signal for providing energy to said uninterruptible power supply means so that said energy can be stored by said uninterruptible power supply means.

8. The apparatus according to claim 1, wherein said means for receiving electrical power from an external power source includes means for correcting the power factor of the computed tomography apparatus as measured from a line input of the apparatus.

9. The apparatus according to claim 1, wherein said means for receiving electrical power from an external power source includes means for rectifying AC power so as to provide DC power.

10. The apparatus according to claim 1, wherein said means for receiving electrical power from an external power source includes means for filtering electromagnetic interference.

11. The apparatus according to claim 1, wherein said means for receiving electrical power from an external power source includes means for protecting the apparatus from excessive electrical currents.

12. The apparatus according to claim 1, wherein said means for receiving electrical power from an external power source includes means for receiving single-phase AC electrical power.

13. The apparatus according to claim 1, further including patient table means for supporting a patient to be medically imaged, and means for providing power transfer from the means for receiving electrical power to the patient table means.

14. The apparatus according to claim 13, wherein said patient table means includes patient table energy means for receiving and storing energy.

15. The apparatus according to claim 14, wherein said patient table energy means for receiving and storing energy includes means for receiving AC electrical power.

16. The apparatus according to claim 1, wherein said external power source is a 115 single phase VAC electrical outlet.

17. The apparatus according to claim 1, wherein said external power source is a 220 VAC three phase electrical outlet.

18. The apparatus according to claim 1, wherein said means for receiving electrical power from an external power source includes:

power factor corrector means for correcting the power factor of the apparatus as measured from the line input of the apparatus, and for providing at least one DC power signal; and converter means, electrically connected to said power factor corrector means, said converter means receiving said at least one DC power signal, and for providing a plurality of regulated DC power signals.

19. The apparatus according to claim 18, further including:

input current sense means, connected to an input of said power factor corrector means, and having a current threshold, said input current sense means for sensing input current provided to said power factor corrector means, and for providing a signal representative of said input current; and protection means, connected to said power factor corrector means and to said input current sense means, for disabling said power factor corrector means when said signal representative of said input current indicates that said current threshold has been exceeded.

20. The apparatus according to claim 18, wherein said converter means includes input voltage sense means having an input voltage threshold, and input current sense means having an input current threshold, said input current sense means sensing input current provided to said converter means, and for providing a signal representative of said input current, and said input voltage sense means sensing input voltage provided to said converter means, and for providing a signal that is representative of said input voltage; and protection means, connected to said converter means, for disabling at least said converter means when either said signal representative of said input current indicates that said input current threshold has been exceeded, or said signal representative of said input voltage indicates that said input voltage threshold has been exceeded.

21. The apparatus according to claim 18, wherein said converter means includes (a) output voltage sense means for sensing output voltage of said converter means and for providing a signal representative of said output voltage, (b) means for establishing a voltage threshold, (c) output current sense means for sensing output current of said converter means and for providing a signal representative of said output current, and (d) means for establishing an output current threshold; and protection means, connected to said converter means, for disabling at least said converter means when either said signal representative of said output current indicates that said output current threshold has been exceeded, or said signal representative of said output voltage indicates that said output voltage threshold has been exceeded.

22. The apparatus according to claim 1, further including a data processor for allocating power between at least said uninterruptible power supply means and said data processor.

23. The apparatus according to claim 22, wherein said data processor allocates power among said uninterruptible power supply means, said data processor, and at least one motor controller.

24. An apparatus according to claim 1, wherein said means for receiving electrical power from an external power source includes means for receiving three-phase AC electrical power.

25. An apparatus according to claim 1, wherein said means for receiving electrical power from an external power source includes means for receiving DC electrical power.

26. An apparatus according to claim 1, wherein said apparatus further comprises a rechargeable power supply mounted to said disk for supplying power to said x-ray source when said disk rotates, and said apparatus further comprises means for charging said rechargeable power supply operative when said disk is stationary and operative by applying power from said means for receiving electrical power from an external power source to said rechargeable power supply.

27. An apparatus according to claim 26, wherein said rechargeable power supply comprises a battery.

28. A computed tomography scanning apparatus including a rotatable disk for rotatable supporting a x-ray source and x-ray detection system for use in generating a scanned image during a scanning operation, the apparatus comprising:

means for receiving electrical power from an external power source, and for providing at least one regulated DC power signal;

means for receiving and storing energy from said regulated DC power signal until at least an amount of energy that is sufficient to complete a scanning operation; and means for applying said energy from said means for receiving and storing energy to said means for receiving electrical power so as to provide an uninterruptible supply of energy for completing a scanning operation without interruption.

29. The apparatus according to claim 24, wherein said means for receiving and storing energy includes rechargeable batteries.

* * * * *